United States Patent [19]

Reyes et al.

[11] Patent Number: 6,165,208
[45] Date of Patent: Dec. 26, 2000

[54] SWEATBAND SYSTEM

[76] Inventors: Blanca Reyes; Martha Reyes, both of 4 Robin La., East Patchogue, N.Y. 11772

[21] Appl. No.: 09/258,334

[22] Filed: Feb. 25, 1999

[51] Int. Cl.[7] .................. A61F 7/00; A61F 7/12
[52] U.S. Cl. ............... 607/112; 607/109; 607/111; 607/98; 607/114; 607/108
[58] Field of Search ............. 607/96, 108, 109, 607/110, 111, 112, 98, 99, 114

[56] References Cited

U.S. PATENT DOCUMENTS

| | | | |
|---|---|---|---|
| 1,567,931 | 12/1925 | Epler . | |
| 3,696,814 | 10/1972 | Umemoto | 128/380 |
| 4,204,543 | 5/1980 | Henderson | 128/402 |
| 4,648,130 | 3/1987 | Kuznetz | 455/351 |
| 4,781,193 | 11/1988 | Pagden | 128/402 |
| 4,915,108 | 4/1990 | Sun | 128/402 |
| 5,165,402 | 11/1992 | McCoy | 128/402 |
| 5,274,865 | 1/1994 | Takehashi | 5/644 |
| 5,395,400 | 3/1995 | Stafford et al. | 607/109 |
| 5,891,189 | 4/1999 | Payne, Jr. | 607/108 |
| 5,931,764 | 8/1999 | Freeman et al. | 482/4 |

*Primary Examiner*—Linda C. M. Dvorak
*Assistant Examiner*—Jocelyn Ram

[57] ABSTRACT

A sweatband system is provided including a band having an inner cloth layer with a heating element mounted therein and connected to a battery pack situated on the band. The band further has an elastomeric outer layer which is defined by an inner face and an outer face which form an interior space for housing a cold pack. The band further includes a pair of ends each with a fastener mounted thereon for securing the band about a body part of a user.

11 Claims, 2 Drawing Sheets

SWEATBAND SYSTEM

BACKGROUND OF THE INVENTION

1. Field of the Invention

The present invention relates to headbands and wristbands and more particularly pertains to a new sweatband system for either heating or cooling a body part of a user while exercising.

2. Description of the Prior Art

The use of headbands and wristbands is known in the prior art. More specifically, headbands and wristbands heretofore devised and utilized are known to consist basically of familiar, expected and obvious structural configurations, notwithstanding the myriad of designs encompassed by the crowded prior art which have been developed for the fulfillment of countless objectives and requirements.

Known prior art headbands and wristbands include U.S. Pat. Nos. 4,648,130; 5,395,400; 4,950,868; 3,254,444; 1,567,931; and Foreign Patents WO 94/14295 and WO 94/09734.

In these respects, the sweatband system according to the present invention substantially departs from the conventional concepts and designs of the prior art, and in so doing provides an apparatus primarily developed for the purpose of either heating or cooling a body part of a user while exercising.

SUMMARY OF THE INVENTION

In view of the foregoing disadvantages inherent in the known types of headbands and wristbands now present in the prior art, the present invention provides a new sweatband system construction wherein the same can be utilized for either heating or cooling a body part of a user while exercising.

The general purpose of the present invention, which will be described subsequently in greater detail, is to provide a new sweatband system apparatus and method which has many of the advantages of the headbands and wristbands mentioned heretofore and many novel features that result in a new sweatband system which is not anticipated, rendered obvious, suggested, or even implied by any of the prior art headbands and wristbands, either alone or in any combination thereof.

To attain this, the present invention generally comprises a headband having a planar configuration with a periphery. The periphery is defined by an elongated linear top edge, a pair of short linear side edges and a bottom edge. As shown in FIG. 2, the bottom edge has a central wide arcuate extent and a pair of tight arcuate extents flanking the central wide arcuate extent. The headband further includes a radio unit mounted thereon adjacent to a second end thereof. A pair of pile fasteners are mounted to one of the ends of the headband for securing the headband about a head of a user. As shown in FIG. 1, the central wide arcuate extent depends over a forehead of the user. Further, the tight arcuate extents depends over ears of the user. For maintaining the headband on the user, a flexible strap has a pair of ends coupled to lower portions of the tight arcuate extents of the headband for encompassing a chin of the user. FIGS. 3 & 4 show at least one wristband with a planar configuration having a periphery defined by an elongated linear top edge, a pair of short side edges and an elongated linear bottom edge. Both the wristband and the headband include an inner terry cloth layer with a serpentinely configured heating coil mounted therein. The heating coil is connected to a battery pack mounted on an outer surface of the band adjacent to a first end thereof. As show in FIG. 4, an elastomeric outer layer of each band is defined by an inner face and an outer face which define an interior space for housing a cold pack. Access to the interior space of the outer layer is gained through a laterally extending slit formed in the outer layer which is selectively sealed by way of ;a pile fastener. The wristband preferably includes a pair of pile fasteners each mounted to one of the ends of the wristband for securing the wristband about a wrist of the user. An illuminated digital clock is mounted on the outer face of the outer layer of the wristband and connected to the battery for displaying a current time. A sleeve is longitudinally mounted on the outer face of the outer layer of the wristband. The sleeve is equipped with an opening for releasably receiving a clip of a pager. Finally, a discreet pocket is formed on the outer face of the outer layer of the wristband which is selectively sealed by way of a pile fastener.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new sweatband system apparatus and method which has many of the advantages of the headbands and wristbands mentioned heretofore and many novel features that result in a new sweatband system which is not anticipated, rendered obvious, suggested, or even implied by any of the prior art headbands and wristbands, either alone or in any combination thereof.

It is another object of the present invention to provide a new sweatband system which may be easily and efficiently manufactured and marketed.

It is a further object of the present invention to provide a new sweatband system which is of a durable and reliable construction.

An even further object of the present invention is to provide a new sweatband system which is susceptible of a low cost of manufacture with regard to both materials and labor, and which accordingly is then susceptible of low prices of sale to the consuming public, thereby making such sweatband system economically available to the buying public.

Still yet another object of the present invention is to provide a new sweatband system which provides in the apparatuses and methods of the prior art some of the advantages thereof, while simultaneously overcoming some of the disadvantages normally associated therewith.

Still another object of the present invention is to provide a new sweatband system for either heating or cooling a body part of a user while exercising.

Even still another object of the present invention is to provide a new sweatband system that includes a band having an inner cloth layer with a heating element mounted therein and connected to a battery pack situated on the band. The band further has an elastomeric outer layer which is defined by an inner face and an outer face which form an interior space for housing a cold pack. The band further includes a pair of ends each with a fastener mounted thereon for securing the band about a body part of a user.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
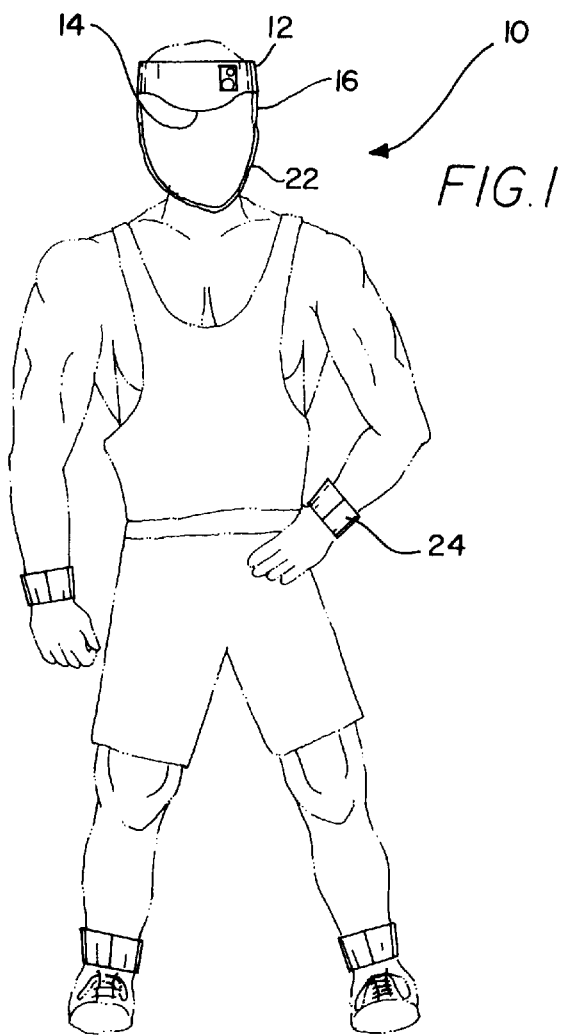
FIG. 1 is a front view of a new sweatband system according to the present invention.

With reference now to the drawings, and in particular to FIGS. 1 through 5 thereof, a new sweatband system embodying the principles and concepts of the present invention and generally designated by the reference numeral 10 will be described.

Figure 2:
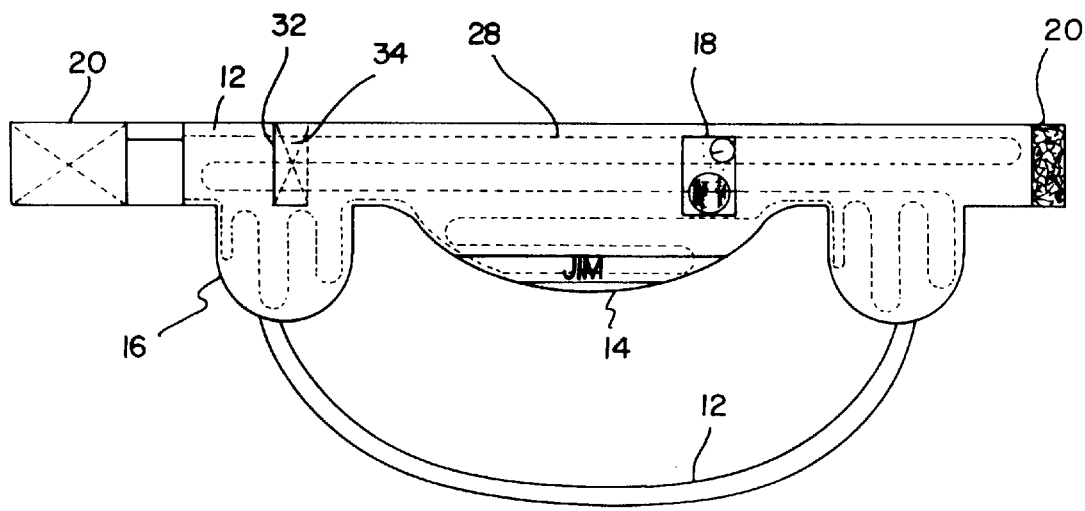
FIG. 2 is a front view of the headband of the present invention.

The present invention, designated as numeral 10, includes a headband 12 having a planar configuration with a periphery. The periphery is defined by an elongated linear top edge, a pair of short linear side edges and a bottom edge. As shown in FIG. 2, the bottom edge has a central wide arcuate extent 14 and a pair of tight arcuate extents 16 flanking the central wide arcuate extent.

The headband further includes a radio unit 18 mounted thereon. The radio unit includes an AM/FM receiver and volume dial. A pair of pile fasteners 20 are each mounted to one of the ends of the headband for securing the headband about a head of a user. As shown in FIG. 1, the central wide arcuate extent depends over a forehead of the user. As an option, the wide arcuate extent may be equipped with any sort of desired indicia. Further, the tight arcuate extents depends over ears of the user. For maintaining the headband on the user, a flexible strap 22 has a pair of ends coupled to lower portions of the tight arcuate extents of the headband for encompassing a chin of the user.

Figure 3:
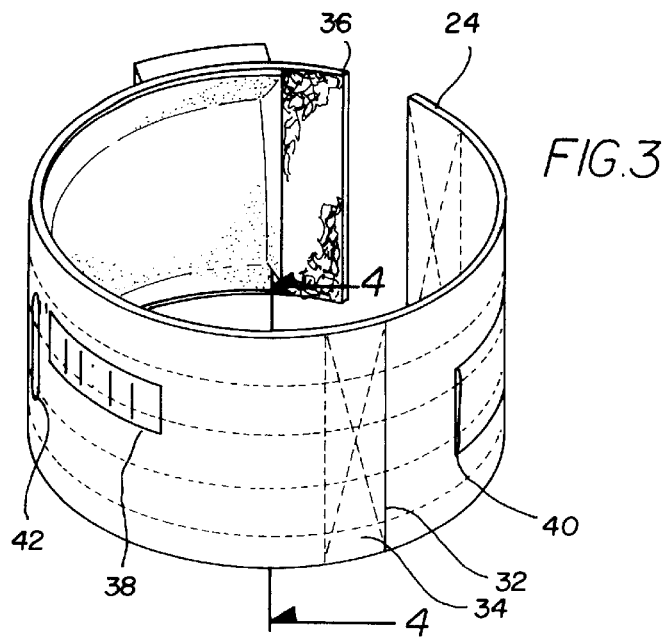
FIG. 3 is a perspective view of the wristband of the present invention.
Figure 4:
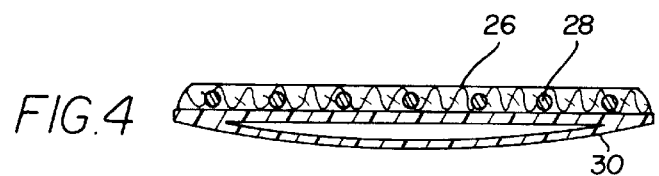
FIG. 4 is a side cross-sectional view of the wristband of the present invention taken along line 4—4 shown in FIG. 3.
Figure 5:
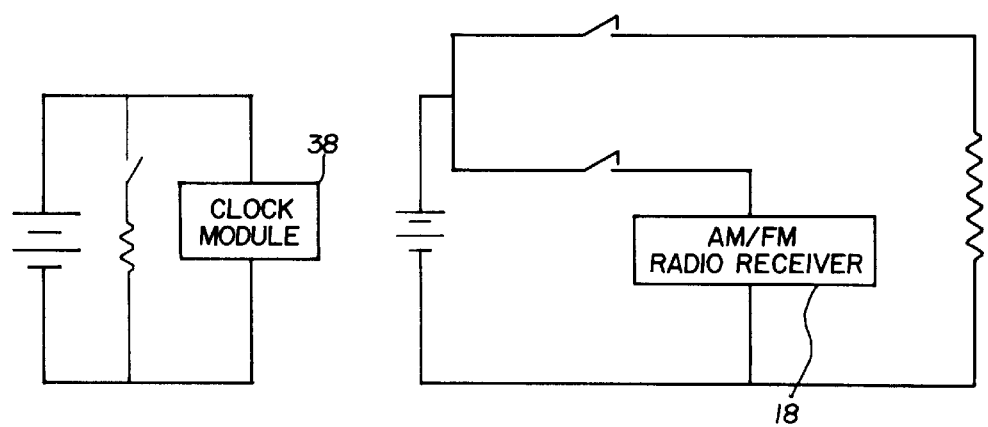
FIG. 5 is a schematic diagram of the present invention.

FIGS. 3 & 4 show at least one wristband 24 with a planar configuration having a periphery defined by an elongated linear top edge, a pair of short side edges and an elongated linear bottom edge. It should be noted that ankle bands may also be employed with structure similar to that of the wristband.

Both the wristband and the headband include an inner terry cloth, wool or foam layer 26 with a serpentinely configured heating coil 28 mounted therein. The heating coil is connected to a battery pack mounted on an outer surface of the band adjacent to a first end thereof. In the preferred embodiment, the heating coil and associated battery of each band has a switch connected therebetween for selectively precluding the flow of power to the coils. As show in FIG. 4, an elastomeric outer layer 30 of each band is defined by an inner face and an outer face which define an interior space for housing a cold pack. Access to the interior space of the outer layer is gained through a laterally extending slit 32 formed in the outer layer which is selectively sealed by way of a pile fastener 34.

The wristband preferably includes a pair of pile fasteners 36 each mounted to one of the ends of the wristband for securing the wristband about a wrist of the user. An illuminated digital clock 38 is mounted on the outer face of the outer layer of the wristband and connected to the battery for displaying a current time. Such illumination may be electrically powered or rely on a chemical illuminescent property. A sleeve 40 is longitudinally mounted on the outer face of the outer layer of the wristband. The pocket is equipped with an opening for releasably receiving a clip of a pager. Finally, a discreet pocket 42 is formed on the outer face of the outer layer of the wristband which is selectively sealed by way of a pile fastener. The discreet pocket may be employed for carrying money or the like.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawing, and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A multiple sweatband system comprising, in combination:

a headband including a planar configuration with a periphery defined by an elongated linear top edge, a pair of short linear side edges and a bottom edge having a central wide arcuate extent and a pair of tight arcuate extents flanking the central wide arcuate extent, the headband including an inner terry cloth layer with a serpentinely configured heating coil mounted therein and connected to a battery pack mounted on an outer surface of the headband adjacent to a first end thereof and an elastomeric outer layer which is defined by an inner face and all outer face which define an interior space for housing a cold pack, wherein access to the interior space of the outer layer is gained through a laterally extending slit formed in the outer layer which is selectively sealed by way of hook and pile fasteners, the headband further including a radio unit mounted on the outer layer adjacent to a second end thereof, a pair of hook and pile fasteners each mounted to one of the ends of the headband for securing the headband about a head of a user such that the central wide arcuate extent depends over a forehead of the user and the tight arcuate extents depending over ears of the user, and a flexible strap having a pair of ends coupled to lower portions of the tight arcuate extents of the headband for encompassing a chin of the user; and at least one wristband with a planar configuration having a periphery defined by an elongated linear top edge, a pair of short side edges and an elongated linear bottom edge, the wristband including an outer elastomeric layer and an inner terry cloth layer, the inner terry cloth layer having a serpentinely configured heating coil mounted therein and connected to a battery pack mounted to an outer surface of the wristband, the elastomeric outer layer being defined by an inner face and an outer face, the outer layer defining an interior space for housing a cold pack, wherein access to the interior space of the outer layer is gained through a vertical slit formed in the outer layer which is selectively sealed by way of hook and pile fasteners, the wristband including a pair of hook and pile fasteners each mounted to one of the ends of the wristband for securing the wristband about a wrist of the user, an illuminated digital clock mounted on the outer face of the outer layer of the wristband and connected to the battery for displaying a current time, a sleeve longitudinally mounted on the outer face of the outer layer of the wristband with an opening for releasably receiving a clip of a pager and a discrete pocket formed on the outer face of the outer layer of the wristband which is selectively sealed by way of hook and pile fasteners.

2. A sweatband system comprising:

a headband and a wrist band, an inner cloth layer, the inner cloth layer having a heating element mounted therein and connected to a battery pack mounted on an outer surface of the band, the elastomeric outer layer being defined by an inner face and an outer face, the outer layer defining an interior space for housing a cold pack, a cold pack adapted for being removably situated in the interior space of the outer layer of the bands, wherein each of the bands includes a pair of ends, each end having a fastener mounted thereon for securing the band about a body part of a user, the fastener on each end of the bands comprising a hook or pile fastener.

3. A sweatband system as set forth in claim 2 wherein access to the interior space of the outer layer is gained through a laterally extending slit formed in the outer layer which is selectively closed by way of a fastener.

4. A sweatband system as set forth in claim 2 wherein the headband includes a radio unit.

5. A sweatband system as set forth in claim 2 wherein a lower edge of the headband includes a central wide arcuate extent that depends over a forehead of the user.

6. A sweatband system as set forth in claim 2 wherein a lower edge of the headband includes a pair of arcuate extents depending over ears of the user.

7. A sweatband system as set forth in claim 6 wherein a lower edge of the headband includes a strap having a pair of ends coupled to the arcuate extents of the headband for encompassing a chin of the user.

8. A sweatband system as set forth in claim 2 wherein the wrist band has a digital clock thereon for displaying a current time.

9. A sweatband system as set forth in claim 2 wherein the wrist band includes a sleeve longitudinally mounted on the band with an opening for releasably receiving a clip of a pager.

10. A sweatband system as set forth in claim 2 wherein a discreet pocket is formed on the headband which is selectively sealed by way of a pile fastener.

11. A sweatband system comprising:

a headband having a periphery defined by an elongated top edge, a pair of side edges and a bottom edge having a central arcuate extent and a pair of side arcuate extents flanking the central arcuate extent, the headband including an inner cloth layer with a heating coil mounted therein and connected to a battery pack mounted adjacent to an outer surface of the headband the headband further including an elastomeric outer layer having an inner face and an outer face, the outer layer defining an interior space for housing a cold pack, wherein access to the interior space of the outer layer is gained through a slit formed in the outer layer which is selectively closed by a hook and pile fastener structure, the headband further including a radio unit, a hook or pile fastener mounted to each of the ends of the headband for securing the headband about a head of a user such that the central arcuate extent depends over a forehead of the user and the side arcuate extents depend over ears of the user, and a flexible strap having a pair of ends coupled to the side arcuate extents of the headband for extending about a chin of the user; and at least one wristband having a periphery defined by a top edge, a pair of side edges and a bottom edge, the wristband including an outer layer and an inner layer, the inner layer having a heating coil mounted therein and connected to a battery pack mounted on the wristband, the outer layer having an inner face and an outer face, the outer layer defining an interior space for housing a cold pack, wherein access to the interior space of the outer layer is gained through a slit formed in the outer layer which is selectively closed by a hook and pile fastener structure, the wristband including a hook or pile fastener mounted to each of the ends of the wristband for securing the wristband about a wrist of the user, a clock mounted on the outer face of the outer layer of the wristband and connected to the battery for displaying a current time, a sleeve formed on the outer face of the outer layer of the wristband with an opening for releasably receiving a clip of a pager and a pocket formed on the outer face of the outer layer of the wristband which is selectively closed by a hook and pile fastener structure.

* * * * *